US010466181B2

(12) United States Patent
Honda et al.

(10) Patent No.: US 10,466,181 B2
(45) Date of Patent: Nov. 5, 2019

(54) FLAW INSPECTION DEVICE AND FLAW INSPECTION METHOD

(71) Applicant: HITACHI HIGH-TECHNOLOGIES CORPORATION, Minato-ku, Tokyo (JP)

(72) Inventors: Toshifumi Honda, Tokyo (JP); Takahiro Urano, Tokyo (JP); Mamoru Kobayashi, Tokyo (JP); Hisashi Hatano, Tokyo (JP); Hironori Sakurai, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 16/085,890

(22) PCT Filed: Mar. 30, 2016

(86) PCT No.: PCT/JP2016/060375
§ 371 (c)(1),
(2) Date: Sep. 17, 2018

(87) PCT Pub. No.: WO2017/168630
PCT Pub. Date: Oct. 5, 2017

(65) Prior Publication Data
US 2019/0094155 A1 Mar. 28, 2019

(51) Int. Cl.
G01N 21/00 (2006.01)
G01N 21/956 (2006.01)
G01N 21/88 (2006.01)
G05B 19/418 (2006.01)
H01L 21/66 (2006.01)

(52) U.S. Cl.
CPC ....... *G01N 21/956* (2013.01); *G01N 21/8806* (2013.01); *G05B 19/41875* (2013.01); *H01L 22/10* (2013.01); *G01N 2201/061* (2013.01)

(58) Field of Classification Search
CPC ............. G01N 21/9501; G01N 21/956; G01N 21/95607; G01N 21/94; G01N 21/8806
USPC ...................................... 356/237.5
See application file for complete search history.

(56) References Cited

U.S. PATENT DOCUMENTS

| 6,985,220 B1 | 1/2006 | Chen et al. | |
| 2012/0229618 A1* | 9/2012 | Urano | G01N 21/9501 348/92 |
| 2014/0198974 A1* | 7/2014 | Takagi | H01L 22/12 382/149 |

FOREIGN PATENT DOCUMENTS

JP 2010286501 A 12/2010

* cited by examiner

*Primary Examiner* — Md M Rahman
(74) *Attorney, Agent, or Firm* — Miles & Stockbridge, PC

(57) ABSTRACT

The present invention aims at providing a defect inspection technique capable of setting parameters used for detecting a defect with a less burden to a user. A defect inspection device according to the present invention receives multiple reference values input by the user and calculates a defect extraction condition so as to optimize an evaluation value calculated with the use of the reference values, the number of actual reports, and the number of false reports (refer to FIG. 8).

15 Claims, 14 Drawing Sheets

FLAW INSPECTION DEVICE AND FLAW INSPECTION METHOD

TECHNICAL FIELD

The present invention relates to a technique for inspecting a defect of an inspection target.

BACKGROUND ART

Patent Literature 1 mentioned below discloses a technique to solve a problem "to detect and analyze characteristics of an inspection piece and identify a defect having level information" as follows. "An inspection system analyzes the level information with the use of a set of initial values of system parameters to capture an initial portion of an abnormality as a defect. The inspection system displays an outline of the captured defect and also displays a movement curve of the potentially captured defect for a threshold parameter. The inspection system selectively changes the parameters to provide a correction threshold, and analyzes the level information on the abnormality with the use of the correction threshold. The inspection system captures an update portion of the abnormality as a defect based on an analysis immediately before the level information and displays the outline of the captured abnormality together with a recalculated movement curve. A step of selectively changing the threshold and recapturing the defect is repeated as desired and a set of corrected threshold parameters is stored for the purpose of being used for prescription of the inspection system (refer to Abstract).

CITATION LIST

Patent Literature

Patent Literature 1: Japanese Unexamined Patent Application Publication No. 2010-286501

SUMMARY OF INVENTION

Technical Problem

In the technique disclosed in Patent Literature 1, the multiple threshold parameters are changed individually to identify the defect and display the movement curvature, to thereby optimize the threshold parameters, individually. However, generally, there are a large number of threshold parameters to be set in the defect inspection device, and it is conceivably burdensome for a user to set those threshold parameters, individually.

The present invention has been made in view of the above problems, and it is an object of the present invention to provide a defect inspection technique capable of setting parameters used for detecting a defect with a less burden to a user.

Solution to Problem

A defect inspection device according to the present invention receives multiple reference values input by a user and calculates a defect extraction condition so as to optimize an evaluation value calculated with the use of the reference values, the number of actual reports, and the number of false reports.

Advantageous Effects of Invention

According to the defect inspection device of the present invention, an effective defect extraction condition can be obtained by only inputting the reference value by the user. As a result, the burden of setting the defect extraction parameter for the user can be reduced.

DESCRIPTION OF EMBODIMENTS

<First Embodiment>

Figure 1:
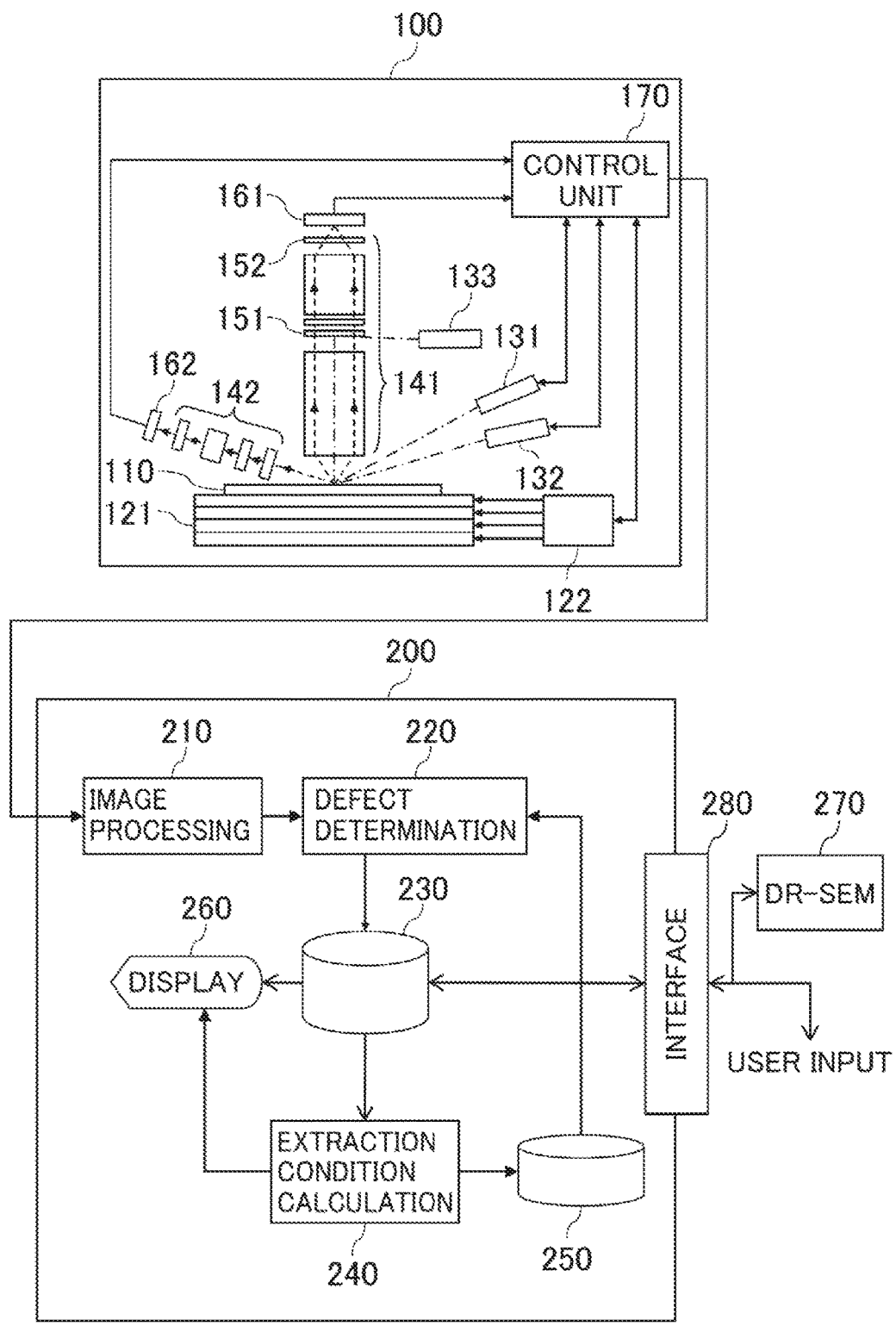
FIG. 1 is a configuration diagram of a defect inspection device 100 according to a first embodiment.

FIG. 1 shows a configuration diagram of a defect inspection device 100 according to a first embodiment of the present invention. The defect inspection device 100 captures an exterior image of a sample 110 and inspects a defect included in the sample 110 with the use of the exterior image. Hereinafter, for the sake of convenience of description, the defect inspection device 100 and an arithmetic device 200 are described separately, but those devices may be integrally formed or interconnected to each other through an appropriate communication line.

The sample 110 is, for example, an object to be inspected such as a semiconductor wafer. A stage 121 can be equipped with the sample 110, move the sample 110 in X, Y and Z directions, and rotate the sample 110. A mechanical controller 122 is a controller for driving the stage 121. One of illumination optical systems 131 and 132 irradiates the sample 110 obliquely with an illumination light. An upward detection system 141 and an oblique detection system 142 form images of scattered light from the sample 110. Image sensors 161 and 162 receive the optical images formed by the respective detection systems and convert the received optical images into image signals. An analyzer 152 is disposed in front of the image sensor 161. The analyzer 152 detects the scattered light while moving the stage 121 in a horizontal direction, thereby being capable of obtaining a two-dimensional image of the sample 110.

A laser or a lamp may be used as a light source of the illumination optical systems 131 and 132. A wavelength of each light source may be a single wavelength or a broadband wavelength light (white light). In the case of using the short wavelength light, an ultraviolet light can be used for the purpose of enhancing a resolution of the image to be detected (detecting a fine defect) In the case of using the laser as the light source, if the laser is a single wavelength laser, the illumination optical systems 131 and 132 may be provided with means for reducing coherence.

An illumination optical system 133 irradiates the sample 110 through an objective lens of the upper detection system 141. An optical path is changed with the use of a folding mirror (not shown) at a position of a spatial filter 151, and the sample 110 can be irradiated from above with the illumination light from the illumination optical system 133. Further, a wavelength plate not shown is placed between each of the illumination optical systems 131 to 133 and the sample 110, thereby being capable of changing a polarization state of the illumination light incident on the sample 110.

The control unit 170 controls the overall operation of the defect inspection device 100 such as the mechanical controller 122, each illumination optical system, and each image sensor. The arithmetic device 200 can be connected to the defect inspection device 100 through the control unit 170. The arithmetic device 200 can control the defect inspection device 100 through the control unit 170.

The arithmetic device 200 includes an image processing unit 210, a defect determination unit 220, an image storage unit 230, an extraction condition calculation unit 240, an extraction condition storage unit 250, and a display unit 260. A DR-SEM 270 may be configured as a function of the arithmetic device 200, or may be configured as a functional unit different from the arithmetic unit 200.

The image processing unit 210 acquires the exterior image of the sample 110 through the control unit 170 and executes processing to be described later with reference to FIG. 3. The defect determination unit 220 extracts the defect of the sample 110 based on the feature amount of the exterior image according to an extraction condition described in extraction condition data stored in the extraction condition storage unit 250. The image storage unit 230 stores a feature amount image representing the feature amount of the sample 110, a determination result by the defect determination unit 220, and so on. The extraction condition calculation unit 240 calculates a new defect extraction condition according to a procedure to be described later, and the defect determination unit 220 extracts the defect with the use of the calculated condition. The display unit 260 displays a processing result by the arithmetic device 200 such as a determination result by the defect determination unit 220 on a screen. A DR-SEM (defect review SEM (scanning electron microscope)) is a device for inspecting the defect of the sample 110 with the use of the SEM image. The DR-SEM is configured as a defect inspection unit different from the defect inspection device 100.

Figure 2:
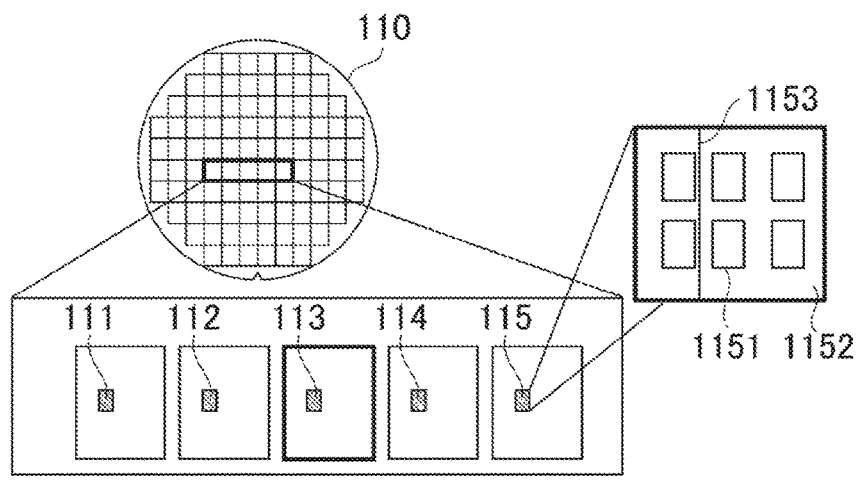
FIG. 2 is a top view showing an example of a sample 110.

FIG. 2 is a top view showing an example of the sample 110. When the sample 110 is, for example, a semiconductor wafer, the same semiconductor chips (dies) 111 to 115 are formed on the sample 110. Memory areas 1151 and a peripheral circuit area 1152 are formed on the semiconductor chip 115. The defect inspection device 100 acquires an exterior image while moving the stage 121 in a direction orthogonal to an illumination line (scan line) 1153. The arithmetic device 200 extracts the defect by comparing the semiconductor chips 111 to 115 with each other, which will be described in detail later.

Figure 3:
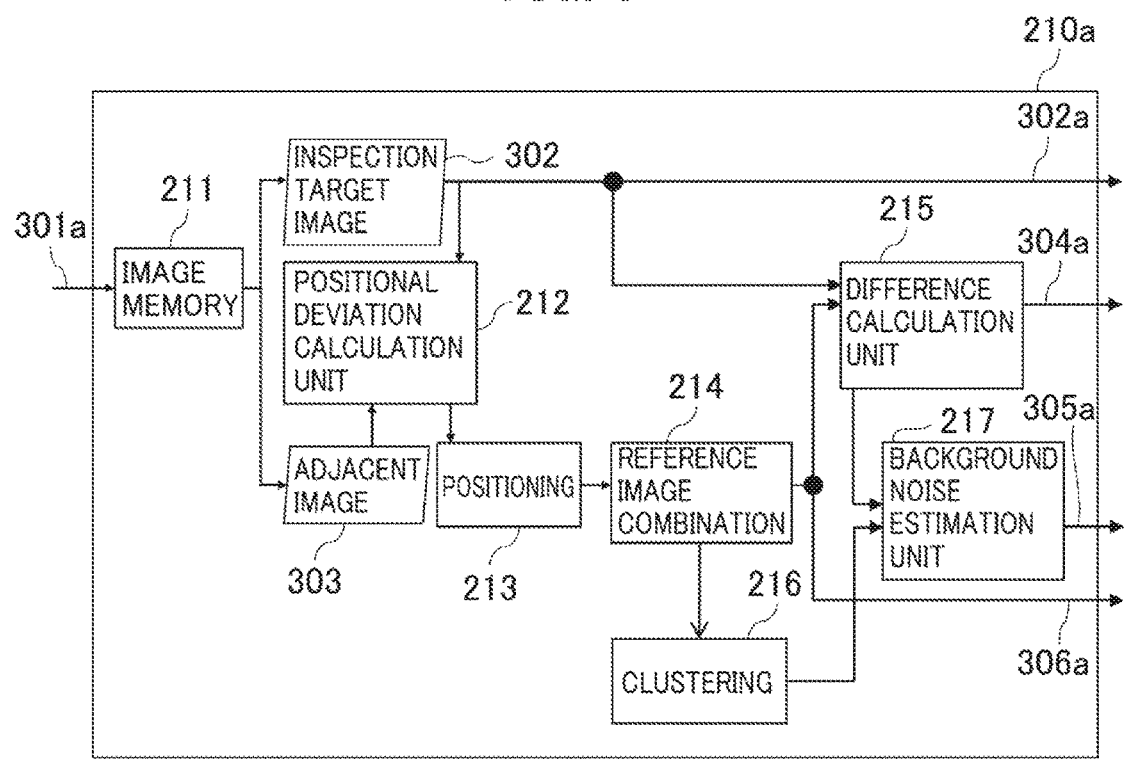
FIG. 3 is a configuration diagram of an internal arithmetic block included in an image processing unit 210.

FIG. 3 is a configuration diagram of an internal arithmetic block included in the image processing unit 210. The image processing unit 210 includes an internal arithmetic block for each detection system included in the defect inspection device 100, and processes the exterior image detected by each detection system, individually. In this example, an internal arithmetic block 210a for processing the exterior image detected by a first detection system (for example, the upper detection system 151) is exemplified Since the other internal arithmetic blocks also have the same structure, when there is a need to distinguish among those internal arithmetic blocks, the subscript of alphabets is used. The same is applied to the drawings to be described later.

The internal arithmetic block 210a receives a pixel value 301a of the exterior image of the sample 110 and accumulates the received pixel value 301a in an image memory 211, thereby generating an inspection target image (for example, the semiconductor chip 111) 302. Similarly, the internal arithmetic block 210a generates adjacent images (for example, semiconductor chips 112 to 115) 303 as comparison targets.

A positional deviation calculation unit 212 calculates, for example, a normalized correlation between the inspection target image 302 and the adjacent images 303, to thereby calculate the amount of positional deviation between both of those images. A positioning unit 213 moves the inspection target image 302 or the adjacent images 303 according to the amount of positional deviation, to align the positions of both of those images. A reference image combiner 214 generates a reference image 306 which is, for example, configured by median values of pixel values (luminance values) of the multiple adjacent images 303. The reference image 306 is an image serving as a reference for defect inspection. A difference calculation unit 215 calculates a difference between the inspection target image 302 and the reference image 306 to create a difference image 304.

A clustering unit 216 clusters partial areas in the reference image 306 into one or more groups based on the pixel values of the reference image 306 and slopes (dl (x, y)/dx, dl(x, y)/dy) of the pixel values. As a result, the partial areas in the reference image 306 is classified into, for example, (a) a group having a large pixel value (bright), (b) a group having a medium pixel value, (c) a group having a small pixel value (dark), and so on. In a process of calculating a difference between the inspection target image 302 and the reference image 306, the difference calculation unit 215 creates a histogram obtained by tallying the difference value and a frequency of the difference value for each of the above groups. For example, the difference calculation unit 215 tallies how far the pixel value belonging to the group (a) is away from the pixel value of the reference image 306, and records a correspondence relationship between the difference value and the frequency as the histogram.

A background noise estimation unit 217 calculates a value representing how much the pixel value of the difference image 304 calculated by the difference calculating unit 215 varies. The value is referred to as background noise. If the reference image 306 and the inspection target image are identical with each other, since there is no difference, the variation is 0 If the difference values between both of those images are various (in the case where the various difference values are present), it is conceivable that a difference between the inspection target image 302 and the reference image 306 is large. The background noise estimation unit 217 obtains a standard deviation of the histogram calculated by the difference calculation unit 215 and sets the obtained standard deviation as a first background noise. The first background noise is meaningful for representing the above-mentioned variation for each of the groups.

The background noise estimation unit 217 further calculates a second background noise based on a variation (for example, standard deviation) of the pixel value at the same place in the multiple adjacent images 303. The second background noise is meaningful for presenting the variation for each of the pixels.

The internal arithmetic block 210a outputs an inspection target image 302a and a reference image 306a. The difference calculation unit 215 disposes the calculated differences in correspondence with the respective pixel positions, to thereby generate and output the difference image 304. The background noise estimation unit 217 generates and outputs a background noise image 305 in which two components of the calculated first background noise and second background noise are disposed in correspondence with the respective pixel positions.

Figure 4:
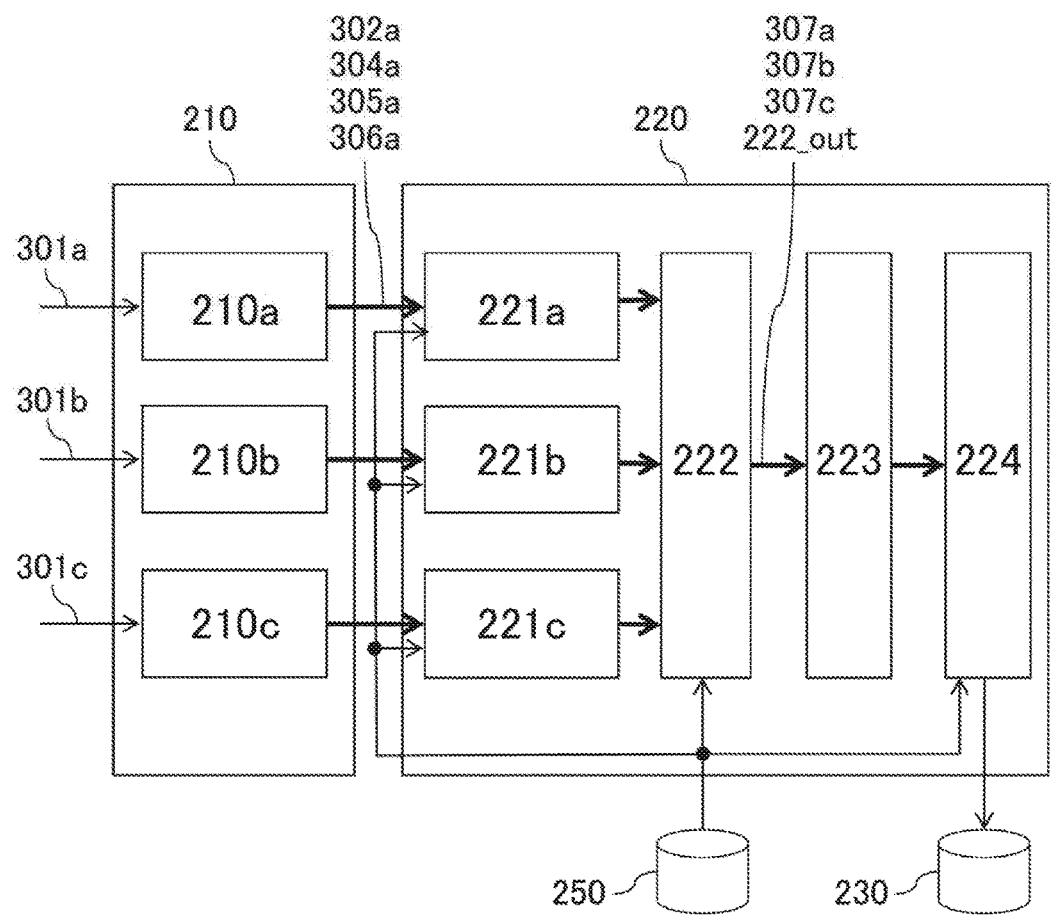
FIG. 4 is a block diagram showing an internal configuration of a defect determination unit 220.

FIG. 4 is a block diagram showing an internal configuration of the defect determination unit 220. The image processing unit 210 includes internal arithmetic blocks (210a to 210c in FIG. 4 assuming that three detection systems are present) for the respective detection systems, and the internal arithmetic blocks execute the processing described with reference to FIG. 3, and deliver outputs to respective normalization units 221a to 221c.

A normalization unit 221 combines components forming the respective pixels of the background noise image, the first background noise, and the second background noise together to calculate a combined background noise at the pixel position. A parameter expressing a formula is stored in the extraction condition storage unit 250 in advance, and used as data. Alternatively, for example, a prescribed arithmetic formula such as an average value may be used. The normalization unit 221 divides the respective pixels of the difference image 304 by the calculated combined background difference image, to thereby calculate a normalized difference image obtained by normalizing the respective pixel values of the difference image 304.

A spatial classifier 222 disposes the pixels of the normalized differential image 304 in a pixel value space having each detection system as a spatial axis and extracts a defect candidate based on a distance between each pixel and an origin. The pixel whose distance from the origin exceeds a threshold is regarded as the defect candidate. The threshold can be stored in advance in, for example, the extraction condition storage unit 250. The threshold can be adjusted as a parameter of the defect inspection device 100. An example of the configuration of the spatial classifier 222 will be described later in FIG. 5.

The feature extraction unit 223 calculates the defect feature amount by analyzing the inspection target images 302a to 302c and the reference images 306a to 306c for the defect candidate extracted by the spatial classifier 222. Examples of the defect feature amount include (a) a shape feature of the defect candidate area (a ratio of a long diameter/a short diameter by elliptic approximation). (b) a total of the normalized differences in the defect candidate area, and (c) a difference of results obtained by subjecting each of the inspection target image 302 and the reference image 306 to a Laplacian filter. The defect candidate area is a partial area defined by a set of pixels determined to be defective and other feature amounts can also be used.

The determination unit 224 separates the defects and the false reports from each other according to the description of the extraction condition data stored in the extraction condition storage unit 250 in a multidimensional space having the normalized difference for each detection system calculated by the normalization unit 221 and each feature amount calculated by the feature extraction unit 223 as spatial axes. The determination unit 224 stores the image of the defect candidate determined to be a defect and the feature amount of the defect candidate in the image storage unit 230.

Figure 5:
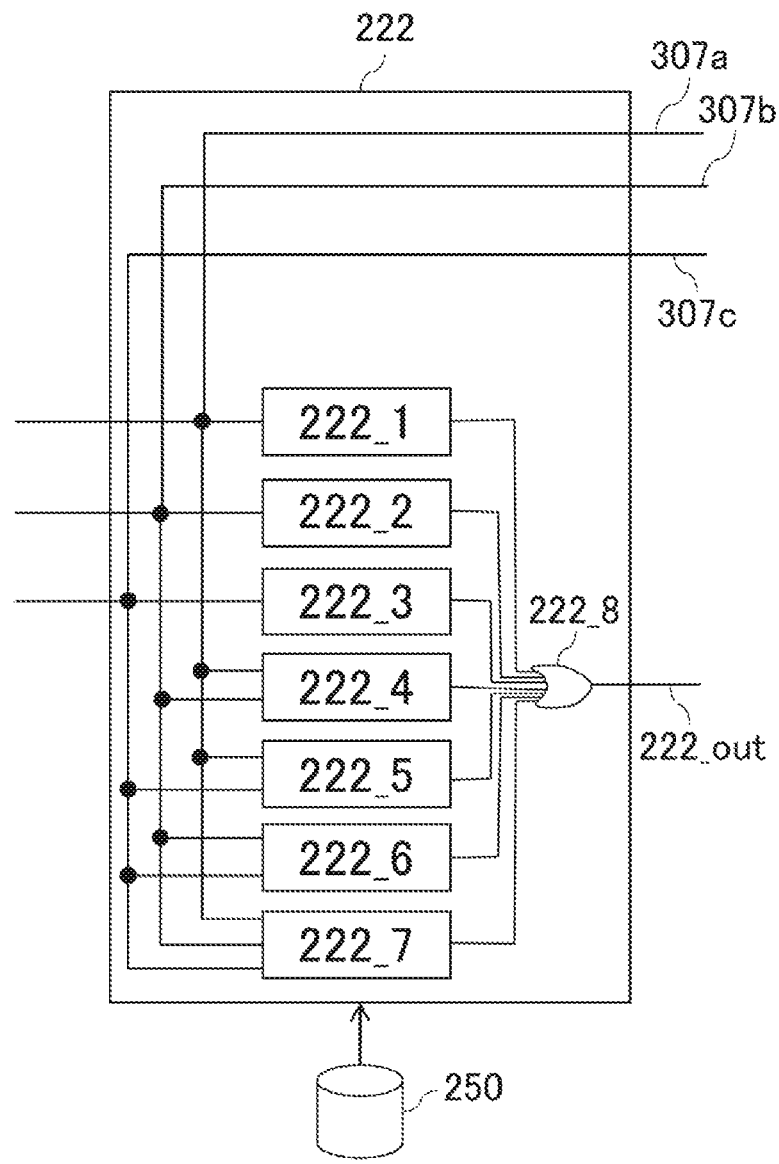
FIG. 5 is a block diagram showing an internal configuration of a spatial classifier 222.

FIG. 5 is a block diagram showing an internal configuration of the spatial classifier 222. The spatial classifier 222 receives each pixel value of the normalized background noise image 305 output from the normalization unit 221 for each detection system (normalized difference pixel values 307a to 307c).

Linear sum calculators 222_1 to 222_3 receive normalized difference pixel values 307a to 307c, respectively, and multiply the normalized difference pixel values 307a to 307c by a predetermined gain (coefficient) When the calculation result exceeds a predetermined threshold, the linear sum calculators 222_1 to 222_3 output a fact that the calculation result exceeds the predetermined threshold to a logical OR unit 222_8. The threshold and the coefficient can be stored in advance in the extraction condition storage unit 250 and further can be adjusted as defect extraction parameters. The same is applied to other linear sum calculators.

The linear sum calculators 222_4 to 222_6 receive pairs of the normalized difference pixel values 307a and 307b, 307a and 307c, and 307b and 307c respectively, multiply the respective normalized difference pixel values by a predetermined coefficient, and add those multiplied normalized difference pixel values together, to thereby obtain a linear sum. When the calculation result exceeds the predetermined threshold, the linear sum calculators 222_4 to 2226 output a fact that the calculation result exceeds the predetermined threshold to the logical OR unit 222_8.

The linear sum calculator 222_7 receives the normalized difference pixel values 307a to 307c and multiplies each normalized difference pixel value by the predetermined coefficient and then adds the multiplied normalized difference pixel values together, to thereby obtain a linear sum. When the calculation result exceeds the predetermined threshold, the linear sum calculator 222_7 outputs a fact that the calculation result exceeds the predetermined threshold to the logical OR unit 222_8.

When receiving the output indicating that the calculation result exceeds the threshold from any one of the linear sum calculators 222_1 to 222_7, the OR unit 222_8 outputs an output indicating that the pixel is defective as the determination result 222_out. In the case where the calculation result is equal to or less than the threshold in all of the logical OR units, the OR unit 222_8 outputs a fact that the pixel is not defective. This process is implemented on all of the pixels, to thereby obtain bit map data indicative of whether each pixel is defective or not.

Figure 6:
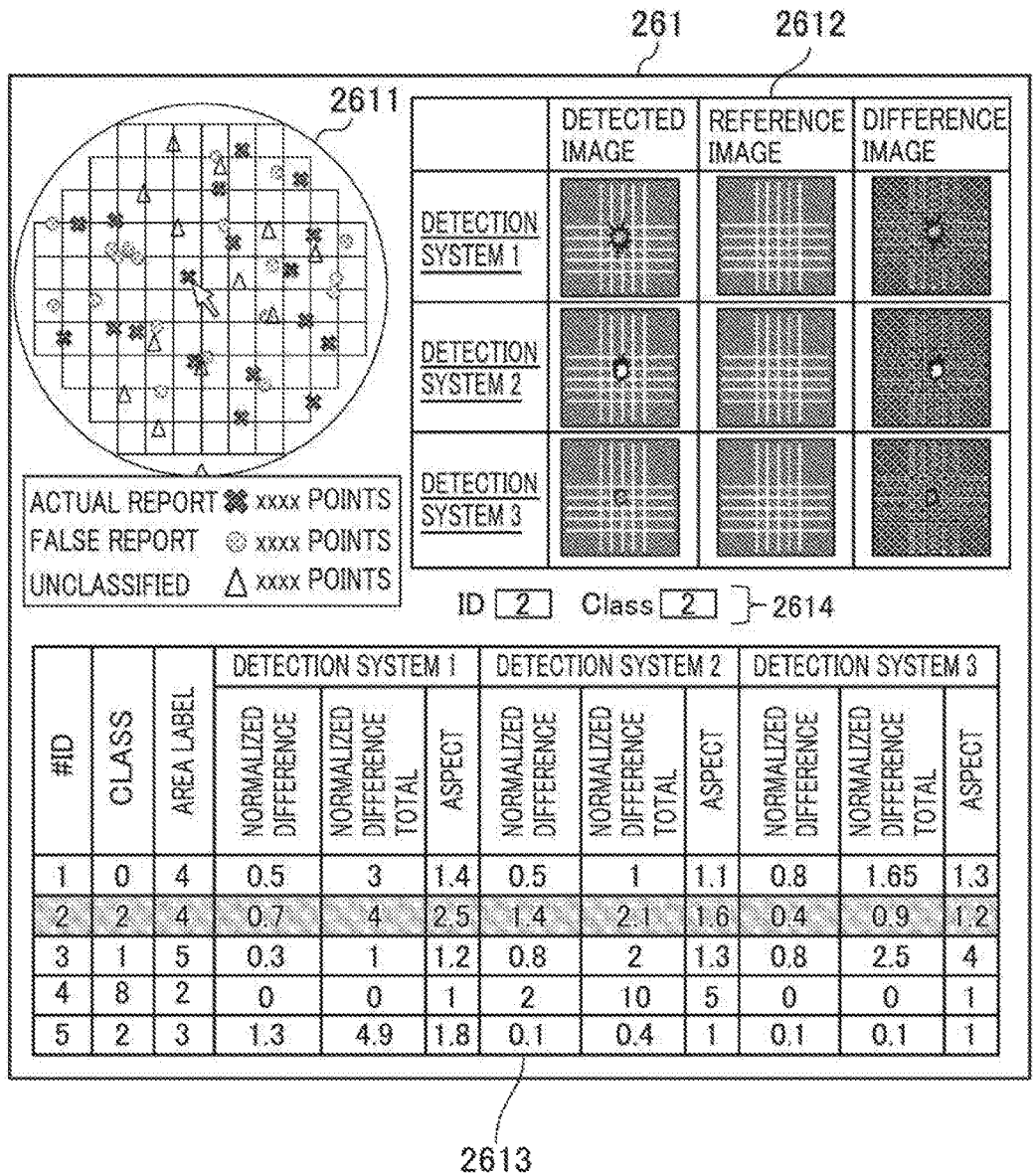
FIG. 6 is a diagram showing an example of a defect candidate screen 261 displayed by a display unit 260.

FIG. 6 shows an example of a defect candidate screen 261 displayed by the display unit 260. A defect map 2611 displays positions of the defect candidates determined to be defective by the determination unit 224 on a top view of the sample 110. A defect candidate image 2612 displays the detection target image 302, the reference image 306, and the difference image 304 for each defect candidate designated (for example, clicked by an arrow pointer) by the user on the defect map 2611. When the external image of the sample 110 is acquired with the use of the multiple detection systems, those images are respectively displayed for the respective detection systems. A defect candidate list 2613 displays the details of the respective defect candidates displayed by the defect map 2611.

The defect candidate list 2613 displays an identifier (ID) of each defect candidate, a defect classification (Class), an area label, and the defect feature amount. The ID is given for convenience in order to distinguish each defect candidate from each other. The defect classification is blank in an initial state. The user checks the defect candidate image 2612 to determine whether the defect candidate is an actual report or a false report, and enters a classification number representing the determination result into an ID column (for example, enter classification=1 if the detect candidate is a false report). A case number column under the defect map 2611 displays the number of defect candidates classified by the user and the number of defect candidates unclassified by the user. Area labels are identifiers representing partial areas of the sample 110. For example, the memory areas 1151 described with reference to FIG. 2 correspond to the area labels. The defect feature amount is a feature amount of the defect candidate extracted by each detection system. The user repetitively selects any defect candidate at random on the defect map 2611 and enters the classification until both of the number of actual reports and the number of false reports reach a certain number of cases, for example.

When designating a specific ID or classification and desiring to display the designated ID and classification on the screen, the user inputs numerical values of the ID and classification to a search condition column 2614. The arithmetic device 200 extracts one of the defect candidates which matches the numerical values and displays the extracted defect candidate in the defect candidate list 2613. Instead of or in addition to the user inputting the classification of each defect candidate, the determination result by the DR-SEM 270 can also be reflected as the classification.

Figure 7:
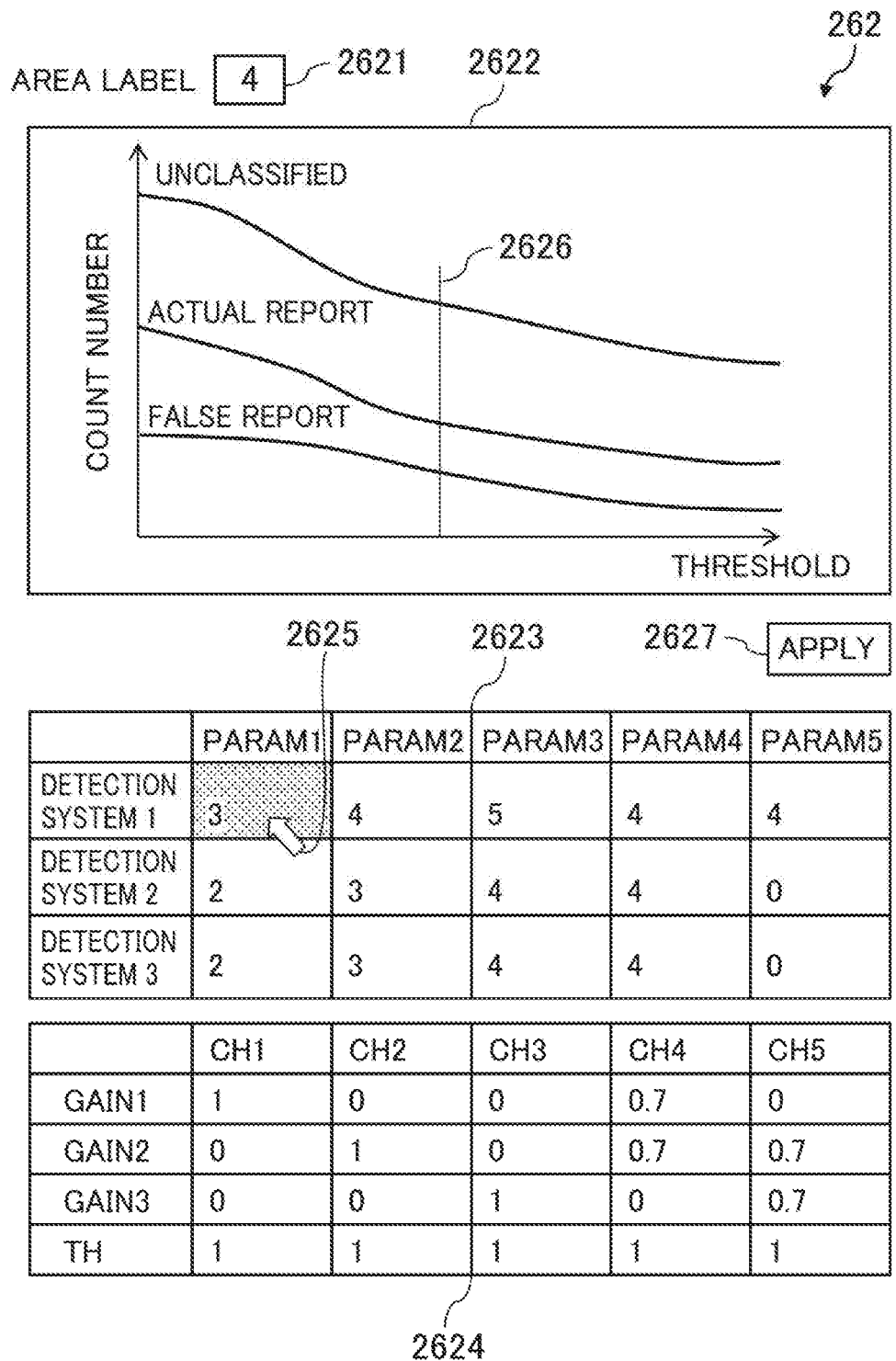
FIG. 7 is a diagram showing an example of a conventional setting screen 262 used by a user to adjust defect extraction parameters.

FIG. 7 shows an example of a conventional setting screen 262 used by the user to adjust the defect extraction parameter. The setting screen 262 is displayed on the display unit 260. The arithmetic unit 200 tallies the number of actual reports and the number of false reports input on the defect candidate screen 261 by the user for each area label, and stores the number of actual reports and the number of false reports in the image storage unit 230. When the user inputs an area label for the area label column 2621, a graph 2622 displays the number of actual reports, the number of false reports, and the number of unclassified reports tallied for the input area label.

A parameter table 2623 is a list of thresholds used when the normalization unit 221 and the determination unit 224 extract the defect for the area label. For example, when a feature amount Param 1 of a certain defect candidate exceeds a threshold 3, the determination unit 224 extracts the defect candidate. A parameter table 2624 is a list of coefficients and thresholds used by the spatial classifier 222. For example, Ch 1 is a coefficient and a threshold used by the linear sum calculator 222_1. The extraction condition storage unit 250 stores those parameters as defect extraction parameters.

The user selects one of the parameters in the parameter table 2623 or the parameter table 2624 with a pointer 2625. The arithmetic device 200 again calculates how the number of actual reports, the number of false reports, and the number of unclassified reports change according to a procedure described in FIGS. 3 to 5 when it is assumed that the selected parameter is changed within a certain range (the range may be also designated by the user). The graph 2622 shows a relationship between a change in parameter and a change in the number of respective detections. The user moves a slider 2626 to designate the parameter value by which a desired number of detections is obtained, and presses an application button 2627. Typically, the user designates the parameter value large in the number of actual reports and small in the number of false reports, but may take the number of unclassified reports into account. A parameter value corresponding to the slider 2626 at the time of pressing the application button 2627 is reflected on the parameter corresponding to the pointer 2625, and the extraction condition storage unit 250 stores the parameter value.

In the case of adjusting the defect extraction parameters according to the procedure as described above, since it is difficult to obtain an optimum defect extraction condition by only adjusting a single parameter, the multiple parameters are changed in parallel through trial and error. Therefore, there is a tendency that it takes a lot of time to adjust the parameters, which is burdensome for the user.

Figure 8:
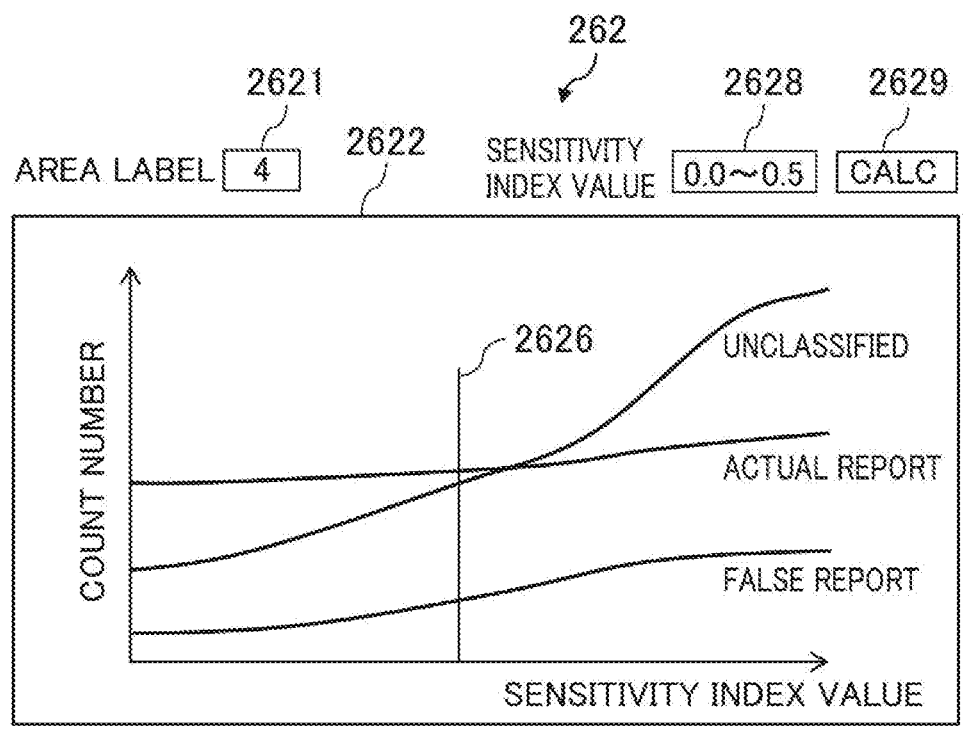
FIG. 8 is a diagram showing an example of a setting screen 262 used by the user to adjust the defect detection parameters according to the first embodiment.

FIG. 8 shows an example of the setting screen 262 used by the user to adjust the defect detection parameters according to the first embodiment. Instead of individually extracting the defect extraction parameters described in FIG. 7, the user enters a range of a sensitivity index value to be described later in an index value column 2628. When the user presses a calculation button 2629, the arithmetic device 200 (the extraction condition calculation unit 240) again calculates the number of actual reports, the number of false reports, and the number of unclassified reports according to the procedure described in FIGS. 3 to 5 while maximizing the evaluation value to be described later. The arithmetic device 200 temporarily stores the defect extraction parameters calculated corresponding to the respective sensitivity index values in the extraction condition storage unit 250. The graph 2622 displays each sensitivity index value and the number of actual reports, the number of false reports, and the number of unclassified reports corresponding to the sensitivity index value.

When the user moves the slider 2626, the arithmetic device 200 reads the defect extraction parameter corresponding to the sensitivity index value pointed by the slider 2626 and displays the read defect extraction parameter in the parameter tables 2623 and 2624. The user moves the slider 2626 to designate the sensitivity index value by which a desired number of detections is obtained, and presses the application button 2627.

The arithmetic device 200 searches for a defect extraction parameter that can maximize the evaluation value Popt(S), for example, according to the following Expression 1. For example, the arithmetic device 200 can implement the search by repetitively changing an element of P until a maximum value of the evaluation value Popt(S) is converged. Symbol P is a vector of the defect extraction parameters (a vector having each coefficient, a threshold, and so on as elements) CountD is the number of actual reports obtained by using the initial value of the defect extraction parameter. CountF is the number of false reports obtained using the initial value of the defect extraction parameter. Cd(P) is the number of actual reports extracted by using the defect extraction parameter vector P. Cf(P) is the number of false reports extracted by using the defect extraction parameter vector P. S is a sensitivity index value input to the index value column 2628. 0 is a small value (negative offset)

[Ex. 1]

$$P_{opt}(S) = \operatorname*{argmaxmin}_{P}\left(Cd(P), S(Count_D + Count_F)\left(\frac{Cd(P)}{Cd(P)+Cf(P)} - o\right)\right) \quad (1)$$

The evaluation value Popt(s) is maximized according to Expression 1 with the result that a calculation process proceeds in a direction of maximizing Cd (P) as a whole. However, when an actual report rate (the number of actual reports/(the number of actual reports+the number of false reports)) is small, a term on a right side of an operator min is selected, as a result of which the possibility of determining that the calculation process has not yet obtained the maximum value is increased. With the action of the above operator, the calculation process that maximizes Cd(P) while maintaining the actual report rate at a somewhat large value can be implemented. The negative offset 0 forcibly selects the right term when the right and left terms within the operator min happen to be equal to each other.

The user only designates how much importance is given to the term on the right side of the operator min in Expression 1 as the sensitivity index value S, thereby being capable of obtaining the optimum defect extraction parameter vector P taking both of Cd (P) and the actual report rate P into account.

The arithmetic device 200 can also set a weight for each classification (Class) of the defect candidates. For example, with the use of a positive value as the weight of the actual report classification and with the use of a negative value as the weight of the false report classification, the evaluation value can increase more as the number of actual reports is larger, and the evaluation value can decrease more as the number of false reports is larger. In that case, Expression 1 is replaced with the following Expression 2. Wdi is the weight of an actual report classification i. Wfi is the weight of the false report classification 8. Cdi(P) is the number of actual reports belonging to the actual report classification i extracted by using the defect extraction parameter vector P. Cfi(P) is the number of false reports belonging to the false report classification i extracted by using the defect extraction parameter vector P.

[Ex. 2]

$$P_{opt}(s) = \operatorname*{argmaxmin}_{P}\left(\sum_i Wd_i Cd_i(P), S(Count_D + Count_F)\left(\frac{\sum_i Wd_i Cd_i(P)}{\sum_i Wd_i Cd_i(P) + \sum_i Wf_i Cf_i(P)} - o\right)\right) \quad (2)$$

Figure 9:
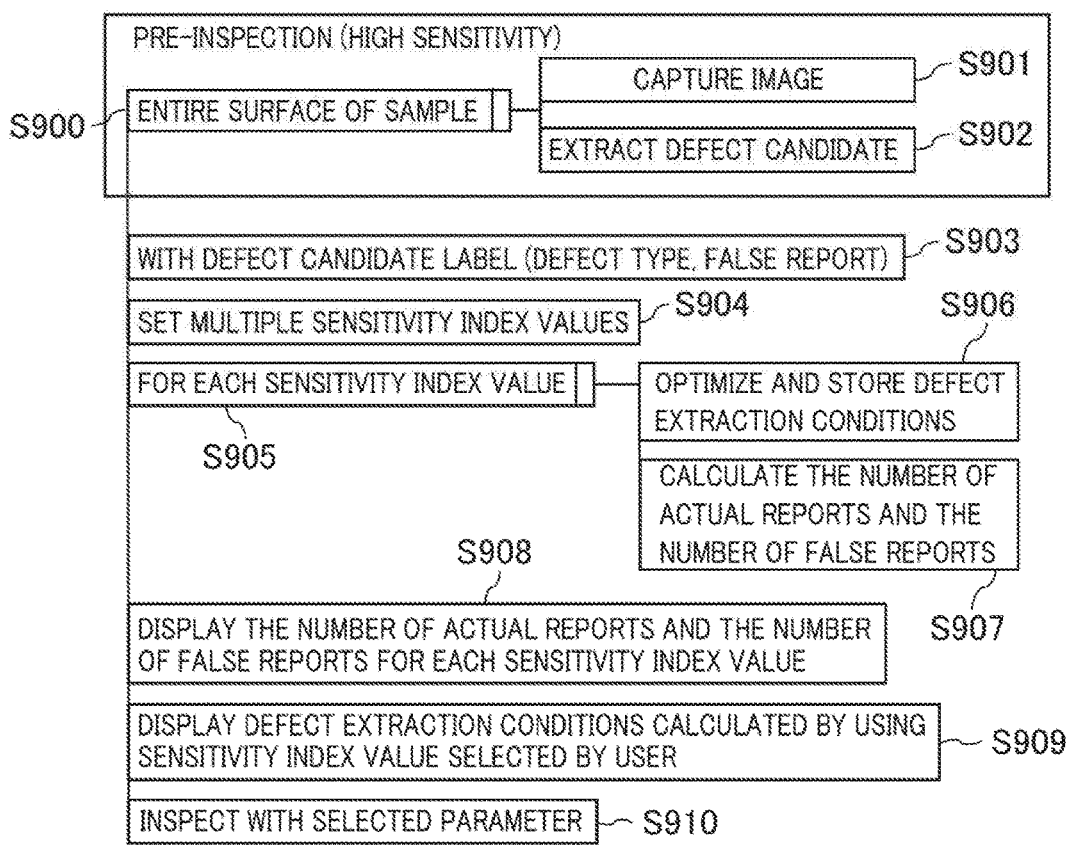
FIG. 9 is a PAD diagram showing a procedure for adjusting the defect extraction parameters by an arithmetic device 200.

FIG. 9 is a PAD diagram showing a procedure for adjusting the defect extraction parameters by the arithmetic unit 200. Hereinafter, each step in FIG. 9 will be described.
(FIG. 9: Steps S900 to S902)

The defect inspection device 100 captures the exterior image of the sample 110 (S 901). The arithmetic device 200 extracts the defect candidates according to the procedure described in FIGS. 3 to 5 (S902). The above process is carried out until an image of an entire surface of the sample 110 is captured, and the defect candidates are extracted (S 900). In those steps, it is desirable to perform a high sensitivity inspection with a relatively large number of false reports so that important defects are detected.
(FIG. 9: Step S903)

The user selects the defect candidate on the defect candidate screen 261 and enters the classification for each defect candidate. In principle, the respective defect candidates are classified into the real report and the false report, but a more detailed defect classification may be given the respective defect candidates. Alternatively, the determination result by the DR-SEM 270 may be used in place of or in combination with the input by the user. The arithmetic device 200 may be appropriately provided with an interface 280 for transmitting and receiving (for example, a communication network) the determination results with respect to the user input (for example, a keyboard or a mouse) or the DR-SEM 270.
(FIG. 9: Steps S904 to S905)

The user inputs the multiple sensitivity index values (or ranges of sensitivity index values) on the setting screen 262 (S904). The arithmetic device 200 performs Steps S906 to S907 for each of the input sensitivity index values (at regular intervals when the range is designated) (S905).
(FIG. 9: Steps S906 to S907)

The arithmetic device 200 optimizes the defect detection parameter according to Expression 1 (Expression 2 in the case of weighting the classification) with the sensitivity index value S as the input parameter and stores the optimized defect detection parameter in the extraction condition storage unit 250 (S906). The arithmetic device 200 calculates the number of actual reports, the number of false reports, and the number of unclassified reports with the use of the defect extraction parameter optimized in Step S906 and the feature amount of each defect candidate (S907).
(FIG. 9: Steps S908 to S910)

The setting screen 262 displays the number of actual reports, the number of false reports, and the number of unclassified reports in the graph 2622 (S908). The user selects the sensitivity index value with the use of the slider 2626 and the arithmetic device 200 displays the defect extraction parameters calculated with the use of the selected sensitivity index value in the parameter tables 2623 and 2624 (S909). When the user presses the application button 2627, the extraction condition storage unit 250 stores the displayed defect extraction parameters, and the arithmetic device 200 thereafter inspects the defects of the sample 110 with the use of the stored defect extraction parameters (S 910).

<Second Embodiment>

In the first embodiment, the description has been given of the configuration example in which the defect extraction parameter corresponding to each sensitivity index value is optimized by designating the range of the sensitivity index values, and the user selects the defect extraction parameter that satisfies a desired requirement from the optimized defect extraction parameters. In a second embodiment of the present invention, a configuration example in which the same processing is performed with the use of parameters other than the sensitivity index values will be described Since the other configuration is the same as that in the first embodiment, in the following description, parameters used in place of the sensitivity index values will be described.

Figure 10:
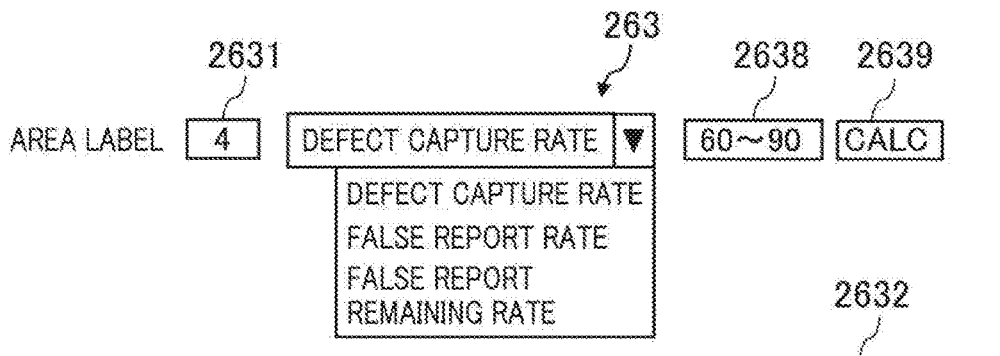
FIG. 10 is a diagram showing an example of a setting screen 263 used by the user to adjust defect detection parameters according to a second embodiment.

FIG. 10 shows an example of a setting screen 263 used by the user to adjust the defect detection parameters according to the second embodiment. The user can use the setting screen 263 instead of or in combination with the setting screen 262. An area label 2631, a parameter table 2633, and a parameter table 2634 are the same as those described with reference to FIG. 8.

The user selects whether the defect extraction parameter is optimized, or not, with reference to any one of the defect capture rate, the false report rate, and the false report residual rate. The defect capture rate is obtained by (the number of actual reports extracted by using the current defect extraction parameter)/(the number of actual reports extracted by using the initial value of the defect extraction parameter). The false report rate is obtained by (the number of false reports)/(the number of actual reports+the number of false reports). The false report residual rate is obtained by (the number of false reports extracted by using the current defect extraction parameter)/(the number of false reports extracted by using the initial value of the defect extraction parameter). Incidentally, the current defect extraction parameters indicate the defect extraction parameters used in S902. The user selects any one of those current defect extraction parameters to be used and further enters a desired range in the index value column 2628. In an example of FIG. 10, the user's instruction is to obtain all of the combinations of the defect extraction parameters whose defect capture rate is a range from 60 to 90. When the user presses the calculation button 2639, the arithmetic device 200 obtains all of the combinations of the defect extraction parameters according to the designation The defect extraction parameters that meet the designation condition can be obtained by, for example, comprehensively searching, or can be obtained by a known search method.

The defect capture rate can also be designated as, for example, 80%, or more, etc. The false report rate can be designated as, for example, 40% or less, etc. The false report residual rate can be designated as, for example, 100/o or less.

The parameter table 2632 displays the defect extraction parameters obtained according to the user's designation and the defect capture rate, the false report rate, and the false report residual rate in the case of using the defect extraction parameters thus obtained. When the user selects any row, the parameter tables 2633 and 2634 display details of the defect extraction parameters corresponding to the selected row.

Figure 11:
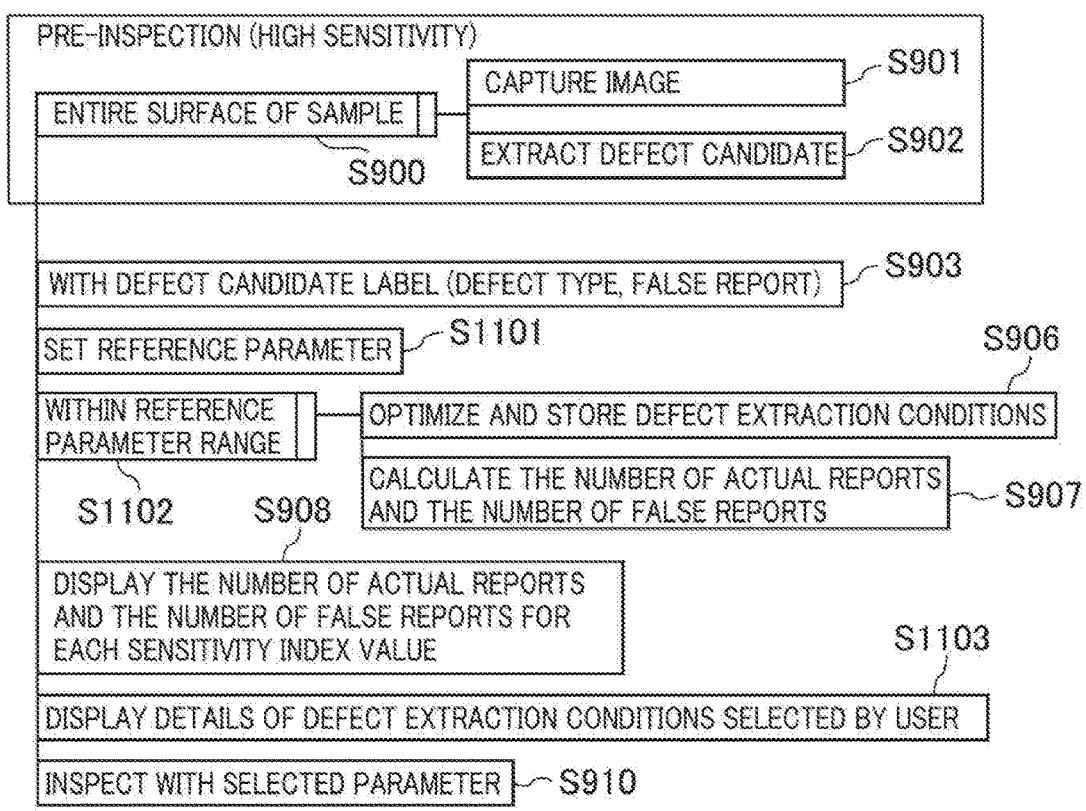
FIG. 11 is a PAD diagram showing a procedure for adjusting the defect extraction parameters by an arithmetic device 200 according to the second embodiment.

FIG. 11 is a PAD diagram showing a procedure for adjusting the defect extraction parameters by the arithmetic device 200 according to the second embodiment. Steps S900 to S903, S906 to S908, and S910 are the same as those in FIG. 9.

(FIG. 11: Step S1101)

The user selects whether the defect extraction parameters are optimized with reference to any parameter on the setting screen 263, and enters the value range (or multiple values) (S1101). The arithmetic device 200 implements Steps S906 to S907 for each of the input reference parameters (at regular intervals when the range is designated) (S1102).

(FIG. 11: Step S1103)

The arithmetic unit 200 displays details of the defect extraction parameters selected by the user on the parameter table 2632 in the parameter tables 2633 and 2634.

<Third Embodiment>

Figure 12A:
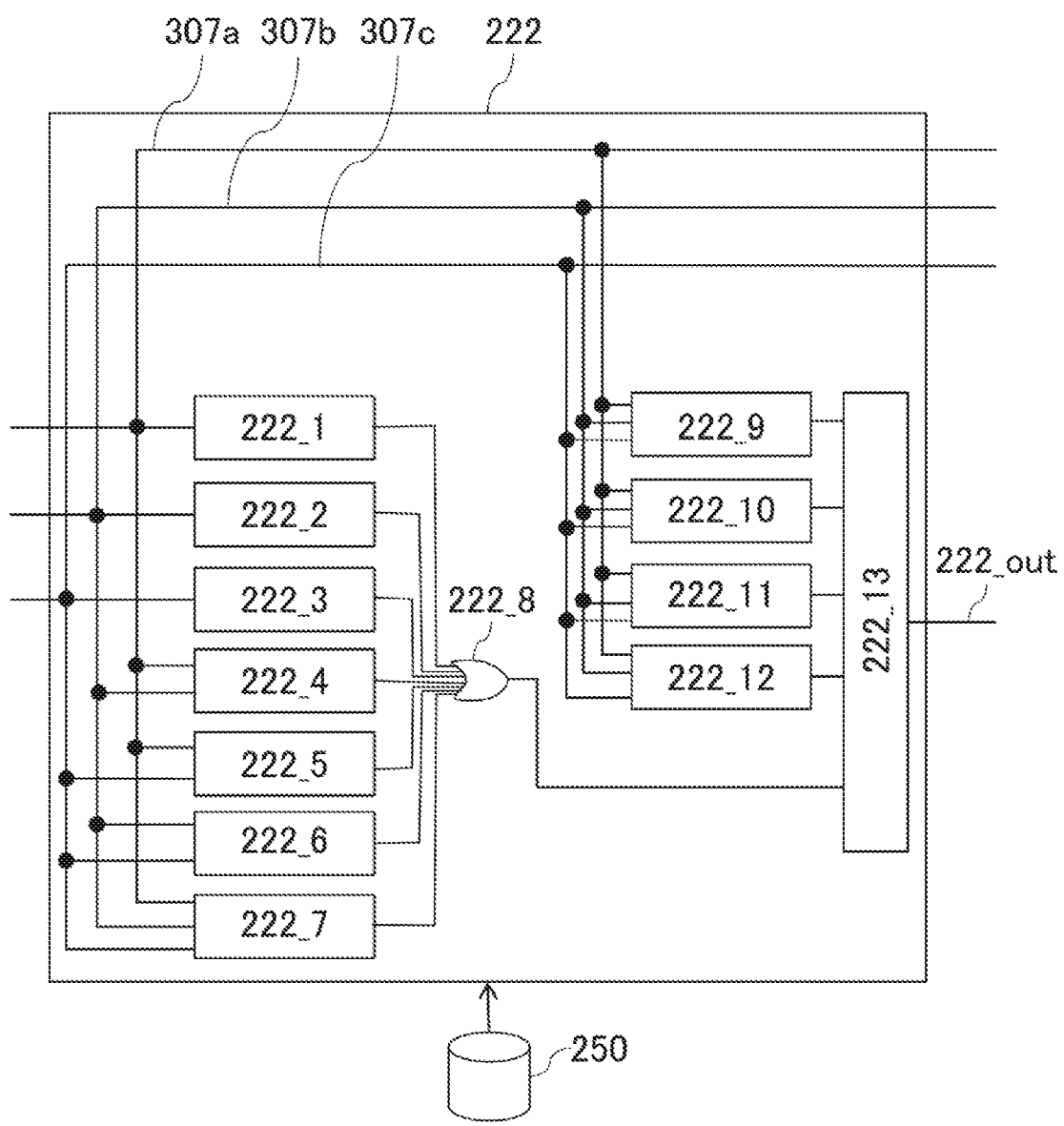
FIG. 12A is a block diagram showing an internal configuration of a spatial classifier 222 according to a third embodiment.

FIG. 12A is a block diagram showing an internal configuration of a spatial classifier 222 according to a third embodiment of the present invention. In the third embodiment, the spatial classifier 222 newly includes internal arithmetic blocks 222_9 to 222_13 in addition to the configuration described in the first embodiment. Hereinafter, differences derived from the addition of those internal arithmetic blocks 222_9 to 222_13 will be described.

Figure 12B:
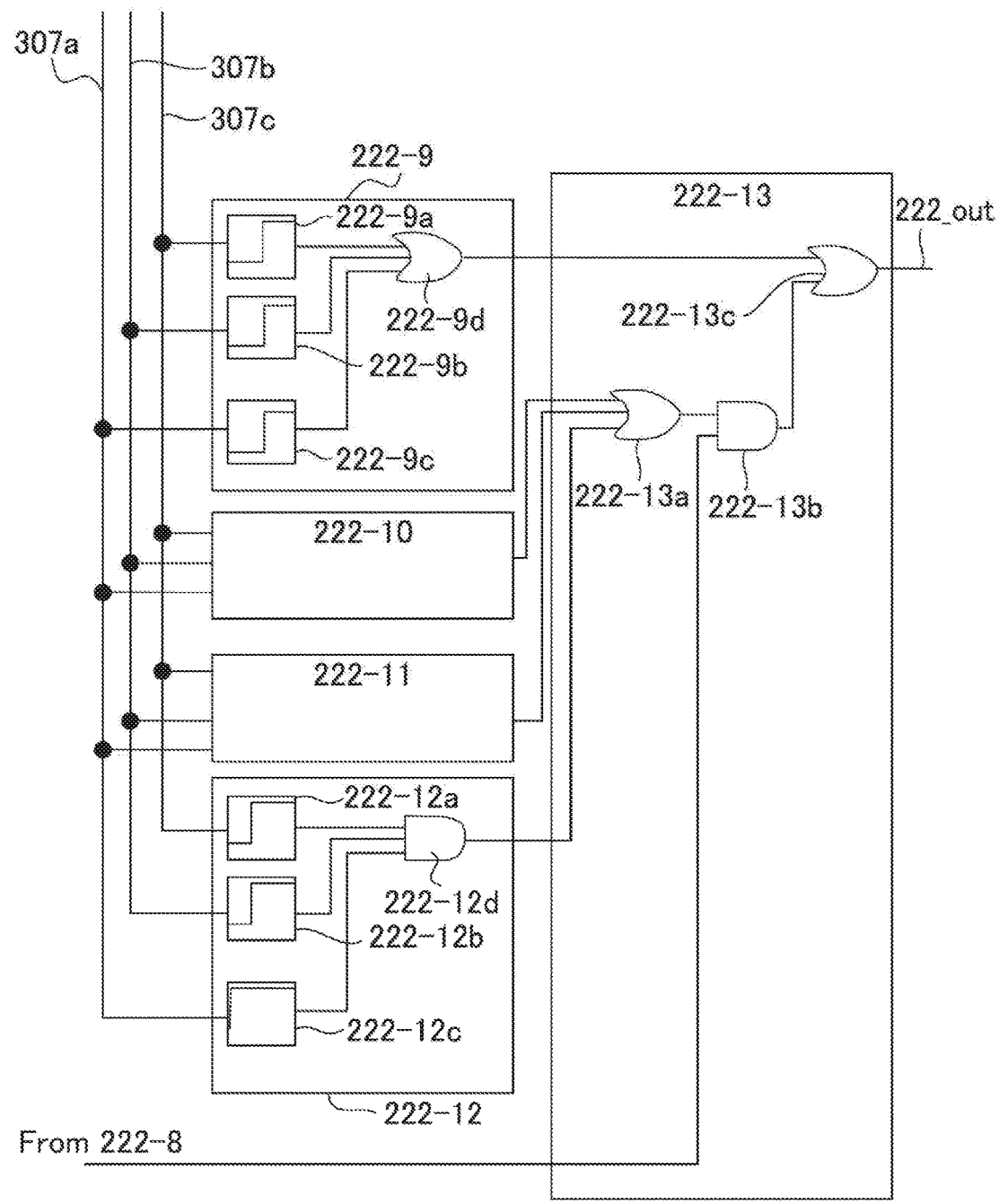
FIG. 12B is a block diagram illustrating details of internal arithmetic blocks 222_9 to 222_13.

FIG. 12B is a block diagram illustrating the details of the internal arithmetic blocks 222_9 to 222_13. The internal arithmetic block 222_9 receives normalized difference pixel values 307*a* to 307*c* and binarization determination units 222-9*a*, 222-9*b*, and 222-9*c* provided in the internal arithmetic block 222_9 determine whether those normalized difference pixel values exceed respective thresholds, or not, individually. The respective thresholds can be set to different values for each of the detection systems. The thresholds are stored as the defect extraction parameters in the extraction condition storage unit 250. The binarization determination result is sent to an OR unit 222-9*d*. When any one of the normalized difference pixel values 307*a* to 307*c* is equal to or larger than the threshold, the OR unit 222-9*d* delivers an output indicating that the pixel is defective to the arithmetic block 222_13.

The internal arithmetic blocks 222_10 and 222_11 perform the same processing as that of the internal arithmetic block 222_12. First, the internal arithmetic block 222_12 will be described. Reference symbols 222-12*a*, 222-12*b*, and 222-12*c* denote binarization determination units provided in the internal arithmetic block 222-12, and have the same function as that of the binarization determination units 222-9*a*. 222-9*b*, and 222-9*c*. Outputs of the binarization determination units 222-12*a*, 222-12*b*, and 222-12*c* are sent to an AND unit 222-12*d*, and the AND unit 222-12*d* determines that there is the defect candidate if all of the normalized difference pixel values 307*a* to 307*c* are equal to or more than the threshold, and delivers the determination result to the internal arithmetic block 222_13. The thresholds used by the binarization determination units 222-12*a*, 222-12*b*, and 222-12*c* are stored in the extraction condition storage unit 250 in advance, and can be further adjusted as the defect extraction parameters.

The internal arithmetic blocks 222_10 and 222_11 have the same function as the internal arithmetic block 222_12, but the thresholds given to the internal binary decision unit are different from those used for the binarization determination units 222-12*a*, 222-12*b*, and 222-12*c*. The threshold value can be stored in advance in the extraction condition storage unit 250 and further adjusted as a defect extraction parameter.

In general, the thresholds applied in the binarization determination units 222-9*a*. 222-9*b*, and 222-9*c* provided in the internal arithmetic block 222_9 are set to be larger than the thresholds used in the internal arithmetic blocks 222_10, 222_11, and 222_12.

The internal arithmetic block 222_13 regards the pixel which is determined to be defective by any one of the internal arithmetic blocks 222_10 to 222_12 to be a defect candidate. The internal arithmetic blocks 222_10 to 222_12 are led to the OR unit 222_13*a* provided in the internal arithmetic block 222_13 to obtain a logical sum. Further, an output of the OR unit 222_3*a* is led to the AND unit 222_13*b*.

The internal arithmetic block 222_13 receives the output from the OR unit 222_8. The AND unit 223_13*b* outputs a pixel determined to be the defect candidate by the OR unit 222_8 and determined to be defective by the OR unit 222_13*a* as the defect candidate. As a result, since only the defects actualized by both of the internal arithmetic blocks 222_1 to 222_8 and the internal arithmetic blocks 222_9 to 222_12 can be extracted, the false report can be prevented. The result of the AND unit 222_13*b* is output to an OR unit 222_13*c*.

Further, different thresholds are used for multilateral verification. The internal arithmetic block 222_12 is based on the assumption that a pixel is defective when the pixel remarkably exceeds the threshold in any detection system. An output of the internal arithmetic block 222_12 is led to the OR unit 222_13c provided in the internal arithmetic block 222_12, and calculates a logical sum with the output of the AND unit 222_13b to output a final defect determination output 222_out. With the use of those components together, the defect candidates can be more accurately extracted.

Figure 13:
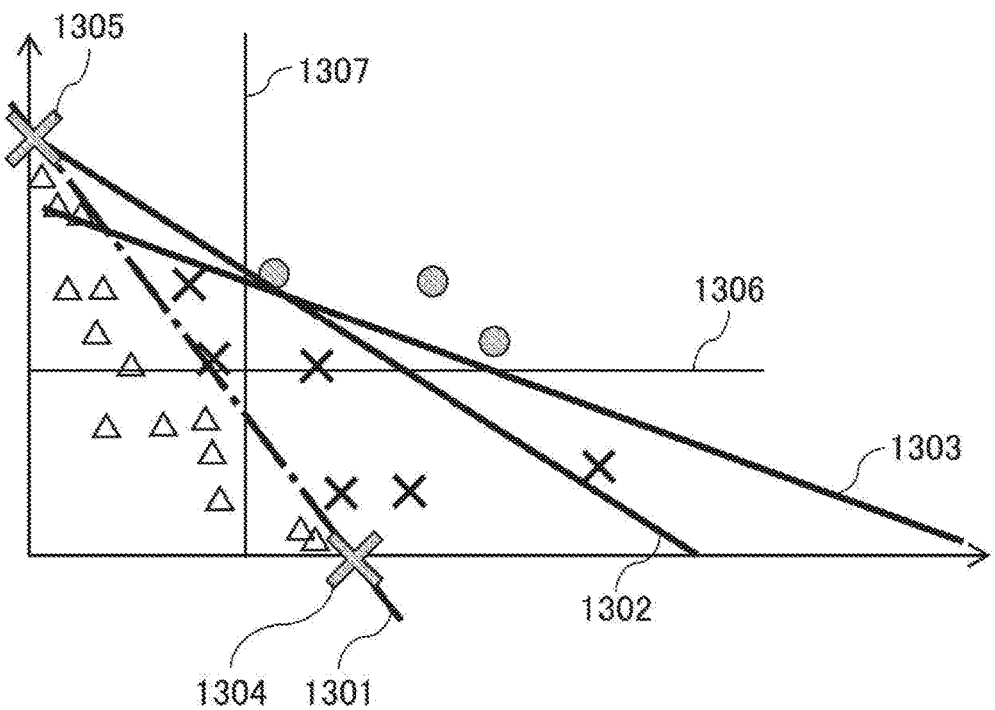
FIG. 13 is a conceptual diagram showing how a spatial classifier 222 separates defects and noise according to the third embodiment.

FIG. 13 is a conceptual diagram showing how the spatial classifier 222 separates defects and noise from each other according to the third embodiment. For convenience of description, an example of a two-dimensional feature amount space having two feature amounts as spatial axes is illustrated Marks O are actual reports, marks x are false reports, and marks A are undetected false reports.

A discrimination plane 1301 is a boundary plane serving as a reference for extracting the defect with the use of an initial value of the defect extraction parameter by the internal arithmetic blocks 222_1 to 222_8. The defect candidates placed above the boundary plane are determined as the defects by the spatial classifier 222. As a result, the marks O and the marks x are determined as the defects.

A discrimination plane 1302 is a boundary plane after the defect extraction parameters have been adjusted. In that case, a part of the marks x and the marks O are determined to be defective. The defect extraction parameters are further adjusted with the results that when the discrimination plane becomes a plane 1303, all of the detected defects on the discriminant plane 1301 can be detected, and all of the false reports can be eliminated. However, on the other hand, since the defect candidates that are not detected in the discriminant plane 1301 are also detected as defects, resulting in a risk of erroneous detection.

In order to avoid the above phenomenon, for example, a virtual false report is generated in segments 1304 and 1305 of the discrimination plane 1301, and a large weight is given to the classification to which those virtual false report belongs so that the defect candidates belonging to the above classification are preferably unlikely to be detected as the actual report. This makes it possible to avoid setting the boundary surface like the discrimination plane 1303.

As another means, it is conceivable to set a new discriminant plane 1306 or 1307 by the internal arithmetic blocks 222_9 to 222_12. As a result, since only the defect candidates in the upper right areas of the discriminant planes 1303, 1306, and 1307 are detected as defects, only the actual reports can be accurately extracted.

<Fourth Embodiment>

Figure 14:
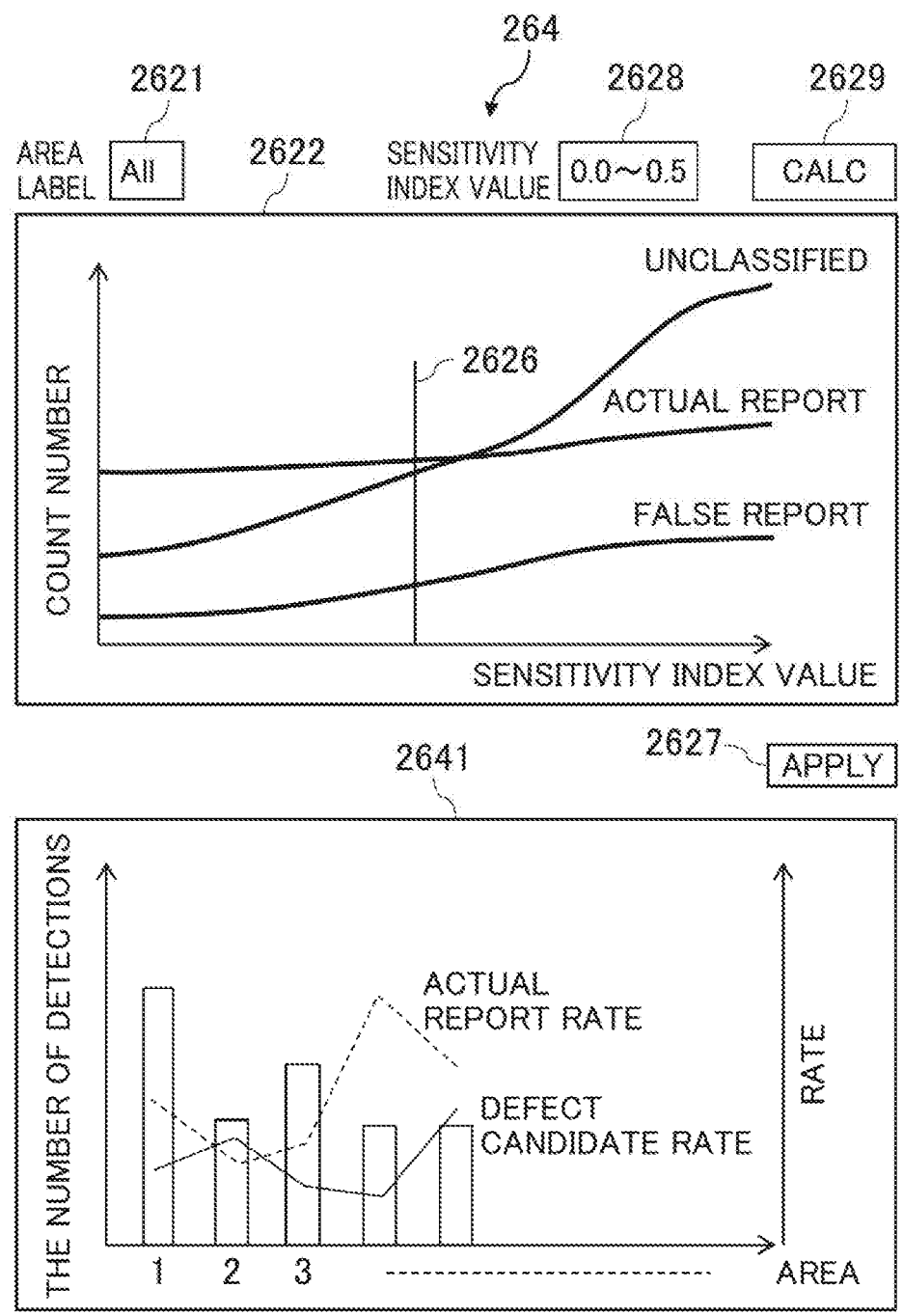
FIG. 14 is a diagram showing an example of a setting screen 264 used by the user to adjust defect detection parameters according to a fourth embodiment.

FIG. 14 shows an example of a setting screen 264 used by a user to adjust defect detection parameters according to a fourth embodiment of the present invention. An upper half of a screen is the same as a setting screen 262. However, a user enters a fact of collectively selecting the entire area in an area label column 2621. The arithmetic device 200 collectively calculates the number of actual reports, the number of false reports, and the like over the entire area label in the same procedure as that in the first embodiment, and a tally column 2641 displays the calculation results. Specifically, the tallying results such as the number of actual reports, the number of false reports, the number of unclassified reports, the actual report rate, the false report rate, the detect capture rate, and the defect residual rate, which are detected, are displayed for the entire area label. Some of the above components may be selectively displayed.

In the fourth embodiment, the comprehensive optimization is performed for the entire area in Expression 1 and Expression 2. As a result, automatic adjustment is performed such that detection sensitivity in an area where the defect is likely to occur is increased, and the detection sensitivity in an area where there are a large amount of false reports is decreased. Since the sensitivity index value can be collectively adjusted over the entire area, the burden of adjusting the defect extraction parameters can be further reduced.

<Fifth Embodiment>

In a fifth embodiment of the present invention, a specific arithmetic expression used by an arithmetic device 200 to detect a defect will be described. The configurations of a defect inspection device 100 and the arithmetic device 200 are the same as those of the first to fourth embodiments.

The condition under which the arithmetic device 200 extracts the defect candidates is expressed by the following Expression 3. Gi is a coefficient used internally by a spatial classifier 222, and is an array of coefficients used by the respective internal arithmetic blocks (seven in FIG. 5). X is an array of feature amount and includes elements of the same number as the number of dimensions of a feature amount space. Thi is a detection threshold.

[Ex. 3]

$$G_1X > Th_1 \lor G_2X > Th_2 \lor \ldots G_nX > Th_n \quad (3)$$

$$G_i = [gi_1 \; gi_2 \ldots gi_m]^T$$

$$X = [x_1 \; x_2 \ldots x_m]^T$$

Expression 3 can be replaced with Expression 4. j is an index of the defect candidate. t(j) is 1 in the case of the actual report and −1 in the case of the false report. class (j) is a classification to which the defect candidate j belongs C ( ) is the cost which is given to an actual report class when no defect is detected, and given to the false report class when a false report is detected. ξi is a slack variable.

[Ex. 4]

$$t(j)K(G_i^T X(j) - Th_i) \geq 1 - C(\text{class}(j))\xi_i \quad (4)$$

In Expression 4, with the replacement with KGi=wi and KThi=bi, the arithmetic device 200 can detect a defect by solving an optimization problem represented by the following Expression 5. J(j) is set to a value of 1 or less if the defect has already been detected when i is other than the current value, and set to 1 if not.

[Ex. 5]

$$w = \operatorname*{argmax}_{w_i} \frac{1}{2}\|w_i\|^2 + C(\text{class}(i))J(j)\sum \xi_i \text{ subject to} \quad (5)$$

$$t(j)(w_i X(j) - b_i) \geq 1 - C(\text{class}(j))J(j)\xi_i$$

<Modifications of the Present Invention>

The present invention is not limited to the embodiments described above, but includes various modifications. For example, the above-mentioned embodiments are described in detail for the purpose of describing the present invention in an easy-to-understand manner. However, the present invention does not always provide all of the configurations described above. Also, a part of one configuration example can be replaced with another configuration example, and the configuration of one embodiment can be added with the configuration of another embodiment. Also, in a part of the respective configuration examples, another configuration can be added, deleted, or replaced independently or in combination.

Also, some or all of the above-described respective configurations, functions, processors, processing means may be realized, for example, as an integrated circuit, or other hardware. Also, the above respective configurations and functions may be realized by allowing the processor to interpret and execute programs for realizing the respective functions. That is, the respective configurations and functions may be realized by software. The information on the program, table, and file for realizing the respective functions can be stored in a storage device such as a memory, a hard disc, or an SSD (solid state drive), or a storage medium such as an IC card, an SD card, or a DVD.

LIST OF REFERENCE SIGNS

100: defect inspection device, 110: sample, 200: arithmetic device, 210: image processing unit, 220: defect determination unit, 230: image storage unit, 240: extraction condition calculation unit, 250: extraction condition storage unit, 260: display unit, 270: DR-SEM

The invention claimed is:

1. A defect inspection device for inspecting a defect of an inspection target, comprising:
   an image generator that generates an exterior image of the inspection target;
   a feature amount calculator that calculates a feature amount of the exterior image;
   a storage device that stores extraction condition data describing an initial value of a condition for extracting the defect of the inspection target;
   a defect determination processor that compares the feature amount with the condition to extract the defect of the inspection target;
   a display that outputs information representing the defect extracted by the defect determination processor; and
   an interface that receives a designation input for designating whether the defect extracted by the defect determination processor is an actual report or a false report,
   wherein the defect determination processor receives a plurality of reference values through the interface and calculates the condition under which an evaluation value calculated using the number of actual reports, the number of false reports, and the reference values becomes optimum for each of the reference values,
   the defect determination processor extracts the defect of the inspection target by using the condition calculated for each of the reference values, and
   the display outputs the condition calculated by the defect determination processor for each of the reference values for each of the reference values and outputs the defects extracted using the conditions calculated for each of the reference values and outputs information representing the extracted defect by using the condition calculated by the defect determination processor for each of the reference values.

2. The defect inspection device according to claim 1, wherein the defect determination processor calculates an actual report rate representing a rate of the number of actual reports to a total of the number of actual records and the number of false reports and calculates the evaluation value by using the actual report rate to extract the defect by using the actual report rate as the condition.

3. The defect inspection device according to claim 2, wherein the defect determination processor receives, as each of the reference values, a numerical value designating a weight of the actual report rate at the evaluation value, and calculates the evaluation value using the weight.

4. The defect inspection device according to claim 1, wherein the defect determination processor classifies the defect of the inspection target according to the feature amount and sets a weight coefficient for each classification of the defect, and
   the defect determination processor sets the weighting coefficient to increase the evaluation value more as the weight coefficient is larger for the classification belonging to the actual report, and decrease the evaluation value more as the weight coefficient is larger for the classification belonging to the false report.

5. The defect inspection device according to claim 1, wherein the defect determination processor receives a numerical value of a defect capture rate indicating a rate of the number of actual reports to the number of actual reports detected by using the initial value of the condition as the reference value, and
   the defect determination processor calculates the evaluation value by using the defect capture rate to extract the defect by using the defect capture rate as the condition.

6. The defect inspection device according to claim 1, wherein the defect determination processor receives a numerical value of a false report rate representing a rate of the number of false reports to a total of the number of actual reports and the number of false reports as the reference value, and
   the defect determination processor calculates the evaluation value by using the false report rate to extract the defect by using the false report rate as the condition.

7. The defect inspection device according to claim 1, wherein the defect determination processor receives a numerical value of a defect residual rate representing a rate of the number of false reports to the number of false reports detected by using the initial value of the condition as the reference value, and
   the defect determination processor calculates the evaluation value by using the defect residual rate to extract the defect by using the defect residual rate as the condition.

8. The defect inspection device according to claim 1, further comprising:
   a plurality of detection systems that acquire a pixel value of the exterior image by imaging the inspection target and deliver the pixel value to the image generator; and
   a difference calculator that calculates a difference between the pixel value of the exterior image acquired by each of the detection systems and a pixel value of a reference image for each of the detection systems,
   wherein the defect determination processor obtains a linear sum of the differences respectively calculated by the difference calculator for one or more of the detection systems, and determines that a pixel corresponding to the difference is defective when the linear sum exceeds a first determination threshold.

9. The defect inspection device according to claim 8, wherein the defect determination processor sets a second determination threshold that is the same as or different from each other for each of the detection systems in advance, and
   the defect determination processor determines that the pixel corresponding to the difference is defective when the linear sum exceeds the first determination threshold and the difference exceeds the second determination threshold for all of the detection systems.

10. The defect inspection device according to claim 1, further comprising:
    a plurality of detection systems that acquire a pixel value of the exterior image by imaging the inspection target and deliver the pixel value to the image generator, and
    a difference calculator that calculates a difference between the pixel value of the exterior image acquired by each of the detection systems and a pixel value of a reference image for each of the detection systems,
    wherein the defect determination processor sets a second determination threshold that is the same as or different from each other for each of the detection systems in advance, and determines that a pixel corresponding to the difference is defective when the difference exceeds the second determination threshold for all of the detection systems.

11. The defect inspection device according to claim 1, wherein the image generator generates the exterior image in each of partial areas of the inspection target and assigns an identifier of each of the partial areas to the exterior image, and
    the defect determination processor extracts the defect of the inspection target for each of the partial areas.

12. The defect inspection device according to claim 1, wherein the image generator generates the exterior image in each of partial areas of the inspection target and assigns an identifier of each of the partial areas to the exterior image, and
    the defect determination processor collectively extracts the defects of the inspection target for all of the partial areas and calculates the evaluation value by using the number of actual reports and the number of false reports for all of the partial areas to optimize the evaluation value for a total of all of the partial areas.

13. The defect inspection device according to claim 1, further comprising:
    a reference image combiner that generates a reference image by combining a plurality of the exterior images of the inspection target together;
    a difference calculation portion of an image processor that calculates a difference between a pixel value of the exterior image and a pixel value of the reference image;
    a clustering portion of the image processor that classifies the defect of the inspection target according to the feature amount;
    a noise estimation portion of the image processor that calculates a variation in the pixel value of the exterior image by using the difference calculated by the difference calculation portion and a classification result by the clustering portion;
    a normalizer that normalizes the variation calculated by the noise estimation portion according to the difference calculated by the difference calculation portion and extracts a defect candidate by comparing the pixel value obtained by the normalization with a first threshold;
    a normalized feature quantity calculator that calculates a feature amount of the defect candidate; and
    a determiner that compares the feature amount calculated by the normalized feature value calculator with a second threshold to further extract a final defect candidate from the defect candidate extracted by the normalizer.

14. The defect inspection device according to claim 1, wherein the defect determination portion receives an instruction to designate which of the conditions calculated for each of the reference values is to be used and extracts the defect of the inspection target by using the designated condition.

15. A defect inspection method for inspecting a defect of an inspection target, comprising:
    an image generation step of generating an exterior image of the inspection target;
    a feature amount calculation step of calculating a feature amount of the exterior image;
    a step of reading detection condition data describing an initial value of a condition for extracting the defect of the inspection target from a storage unit;
    a defect determination step of comparing the feature amount with the condition to extract the defect of the inspection target,
    an output step of outputting information representing the defect extracted in the defect determination step, and
    a step of receiving a designation input for designating whether the defect extracted in the defect determination step is an actual report or a false report,
    wherein the defect determination step further receives a plurality of reference values and calculates the condition under which an evaluation value calculated using the number of actual reports, the number of false reports, and the reference values becomes optimum for each of the reference values,
    the defect determination step further extracts the defect of the inspection target by using the condition calculated for each of the reference values, and
    the output step further outputs the condition calculated in the defect determination step for each of the reference values and outputs information representing the defect extracted in the defect determination step by using the condition calculated for each of the reference values.

* * * * *